United States Patent [19]
Keyes

[11] Patent Number: 5,709,673
[45] Date of Patent: Jan. 20, 1998

[54] FLUSHABLE OSTOMY POUCH

[75] Inventor: Denis E. Keyes, Rocky Hill, N.J.

[73] Assignee: E.R.Squibb & Sons, Inc., Princeton, N.J.

[21] Appl. No.: 371,671

[22] Filed: Jan. 12, 1995

Related U.S. Application Data

[63] Continuation of Ser. No. 14,950, Feb. 8, 1993, abandoned.

[51] Int. Cl.⁶ ........................................................ A61F 5/44
[52] U.S. Cl. .................................................... 604/332
[58] Field of Search ................................ 604/332–345

[56] References Cited

U.S. PATENT DOCUMENTS

| | | | |
|---|---|---|---|
| 4,095,599 | 6/1978 | Simonet-Haibe | 604/336 |
| 4,393,080 | 7/1983 | Pawelchak et al. | 604/336 |
| 4,681,574 | 7/1987 | Eastman | 604/344 |
| 4,946,720 | 8/1990 | Oishi et al. | 604/332 |
| 5,009,648 | 4/1991 | Aronoff et al. | 604/332 |
| 5,110,390 | 5/1992 | Martini et al. | 604/332 |

FOREIGN PATENT DOCUMENTS

| | | | |
|---|---|---|---|
| 2525897 | 11/1983 | France | 604/332 |
| 2083762 | 3/1982 | United Kingdom | 604/332 |

Primary Examiner—Robert A. Clarke
Attorney, Agent, or Firm—Stuart E. Krieger

[57] ABSTRACT

The ostomy pouch has a coupling or securement member formed as a washer-shaped wafer of adhesive material, preferably a hydrocolloid. The pouch is secured directly onto the abdominal wall with the adhesive wafer aligned with the stoma. Flushability of the pouch is enhanced by forming the pouch with converging side walls within an optimum angular range and a predetermined pouch width and pouch height. The pouch also has a predetermined wall thickness and the wafer is of predetermined thickness. Thus when the pouch is deposited in a water-saver toilet, bottom end first in a carrier sleeve, the pouch can flow in streamlined fashion through the passages of a toilet and any sewer pipe or septic line connected to the toilet. If the flush capacity of the toilet and the flow rate of water through the toilet and sewer line are increased, the ostomy pouch can be deposited in the toilet without a carrier sleeve.

12 Claims, 2 Drawing Sheets

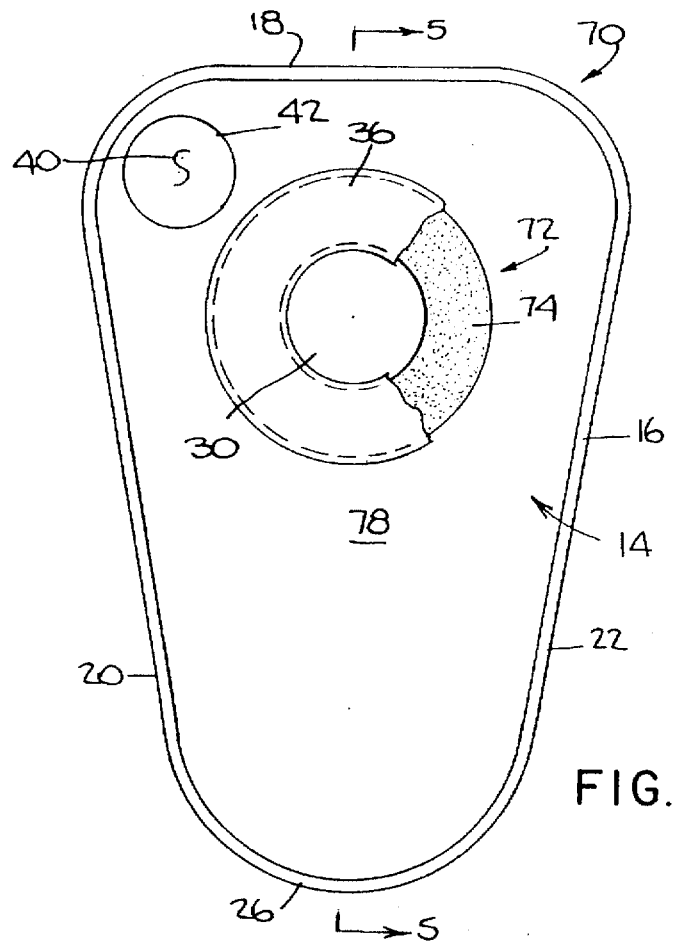
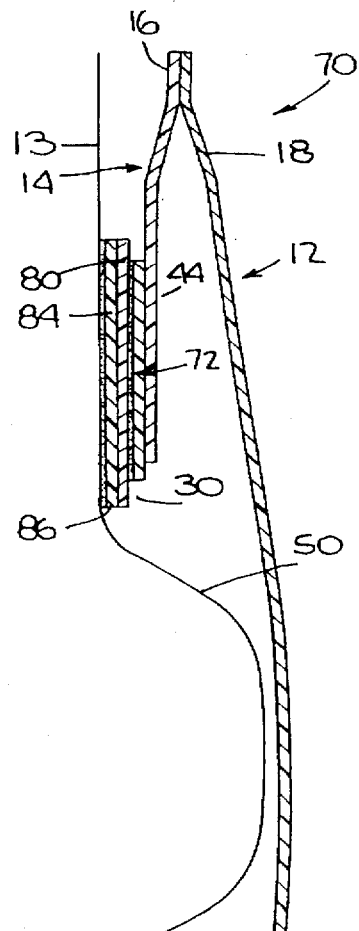
FIG. 4
FIG. 5
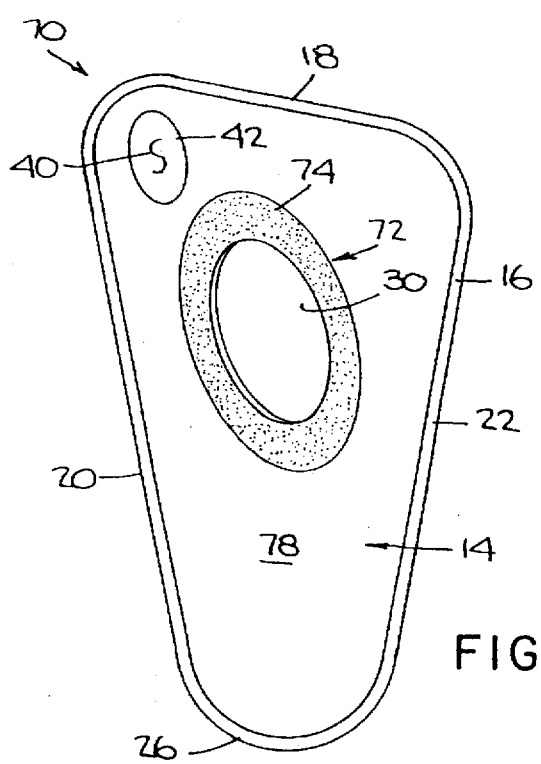
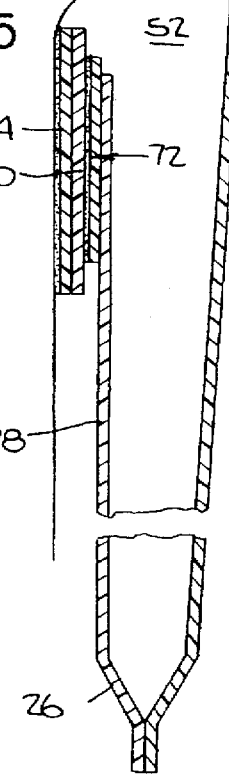
FIG. 6

FLUSHABLE OSTOMY POUCH

This is a continuation of application Ser. No. 08/014,950, filed Feb. 8, 1993, now abandoned.

BACKGROUND OF THE INVENTION

This invention is directed to ostomy pouches and more particularly to a novel flushable ostomy pouch.

One of the inconveniences associated with ostomy care is the disposal of the waste collection pouch or ostomy pouch after it has been used. Toilet flushing of the pouch is a most generally sought means of disposal. However major problems in flushing an ostomy pouch down a toilet are trapped air within the pouch that creates buoyancy and structural features of the pouch that can cause the pouch to become trapped in the flow passages of the toilet or in a connecting pipe or sewer line.

For example, the pouch shown in U.S. Pat. No. 4,490,145 has a face plate with an adhesive layer for coupling or securing the pouch to the abdomen such that the waste inlet opening aligns with the stoma. The face plate and the adhesive coating are usually approximately 35 mils thick and the pouch material is usually approximately 75 microns thick. Although the pouch envelope and the face plate are flexible in a general sense, they have been found to lack sufficient flexibility to adequately negotiate the flow passages of a water-saver type toilet, which uses less water than a standard flush toilet.

Pouch configurations which may be flushable in standard toilets with standard flush capacity often do not perform satisfactorily in water-saver type toilets and occasionally perform inconsistently in standard flush toilets.

One known response to ostomy pouch flushing problems such as pouch trappage and clogging is to form the ostomy pouch of material that softens and becomes slimy or slippery when contacted with water, to promote flowage in a water passage or pipeline.

While a pouch that becomes slimy or slippery upon immersion in water may have enhanced slidability against wall surfaces of toilets and sewer lines, the contact of such material against the body can be uncomfortable if it becomes wet while it is worn. Such pouches are likely to discourage a user from engaging in swimming and other physical activity and generally require protective covering while showering. Furthermore, pouches formed of water reactive material may still cause clogging in water-saver toilets with relatively low volume flush capacity.

Another known structure that facilitates flush disposal of ostomy pouches is that of U.S. Pat. No. 4,830,187, which shows a plastic carrier sleeve or bag into which a pouch can be placed before flush disposal. The sleeve or bag forms a slimy or slippery layer when exposed to water, thereby sliding on surfaces that might otherwise cause snagging of the pouch. However, since the carrier sleeve conforms to the pouch during flushing, a pouch that is not flexible enough to negotiate the flow passages in a toilet may still become trapped even with a slippery carrier sleeve.

It is thus desirable to provide an ostomy pouch that is adapted to easily flush down a toilet, even a water-saver toilet, and which has an optimum height, width and convergence angle to facilitate flush disposal.

OBJECTS AND SUMMARY OF THE INVENTION

Among the several objects of the invention may be noted the provision of a novel ostomy pouch, a novel ostomy pouch that can be disposed of by flushing down a toilet, a novel ostomy pouch with an adhesive coupling that is structured to permit flushability of the pouch, an ostomy pouch with a novel envelope configuration that enhances flushability of the pouch, a novel ostomy pouch having a converging streamlined shape with an optimal angle of convergence and an optimal dimensional relationship between top width, height and angle of convergence to facilitate flush disposal, and a novel method for facilitating flush disposal of an ostomy pouch.

Other objects and features of the invention will be in part apparent and in part pointed out hereinafter.

In accordance with the invention, the flushable ostomy pouch includes an envelope formed of flexible plastic sheet material that defines a chamber for collection of body waste from a stoma. A waste inlet opening is formed in the pouch to receive waste material that passes from the stoma into the collection chamber. Coupling or securing means are provided on the pouch at the waste inlet opening for joining the pouch to the abdominal wall with the waste inlet opening positioned to align with the stoma.

In one embodiment of the invention, the coupling means is a washer-shaped adhesive wafer preferably formed of a hydrocolloid material for adhering the pouch directly onto the abdominal wall around the stoma.

The shape of the pouch, the thickness of the pouch envelope and the thickness of the adhesive coupling wafer are selected to enable the pouch to negotiate the passages of a water-saver toilet and facilitate flow through the sewer pipe and septic lines.

Preferably the pouch has opposite side edges that converge from the top portion to the bottom portion such that the pouch in plan view is substantially V-shaped. The top width, pouch height and convergence angle are of a predetermined magnitude to provide a streamlined shape and assure optimum flushability of the pouch in a water-saver toilet.

The pouch is placed bottom end down for flushing and is preferably deposited in a known sleeve or bag that becomes slippery upon contact with water when flushed down a water-saver toilet. When the ostomy pouch is used with European type wash down water closets, the carrier sleeve or bag can be omitted. However, the top portion of the pouch can be cut or otherwise ripped to permit evacuation of the contents of the collection chamber in European wash down water closets.

In another embodiment of the invention, the coupling means is a washer-shaped adhesive coupling tape joined to the pouch envelope around the waste inlet opening for engagement with a coupling film provided on an abdominal mounting plate. The abdominal mounting plate includes a stomal aperture that aligns with the waste inlet opening of the ostomy pouch. The pouch is separated from the mounting plate by peeling the coupling tape from the coupling film on the mounting plate. The adhesive bond between the coupling tape and the coupling film is selected to resist direct pull off of the pouch from the mounting plate but permits peeling removal thereof.

This pouch is dimensionally similar to the first embodiment and is thus substantially V-shaped with side edges that converge from the top portion of the envelope to the bottom portion. Flush disposal of the pouch is thus accomplished in a manner similar to that described for the first embodiment.

The invention accordingly comprises the constructions and method hereinafter described, the scope of the invention being indicated in the claims.

DESCRIPTION OF THE DRAWINGS

In the accompanying drawings,

FIG. 4 is a plan view of a further embodiment of the invention;

FIG. 5 is a sectional view thereof taken on the line 5—5 of FIG. 4; and,

FIG. 6 is a simplified perspective view thereof, with the adhesive face of the support coupling exposed.

Corresponding reference characters indicate corresponding parts throughout the several views of the drawings.

DETAILED DESCRIPTION OF THE INVENTION

Figure 1:
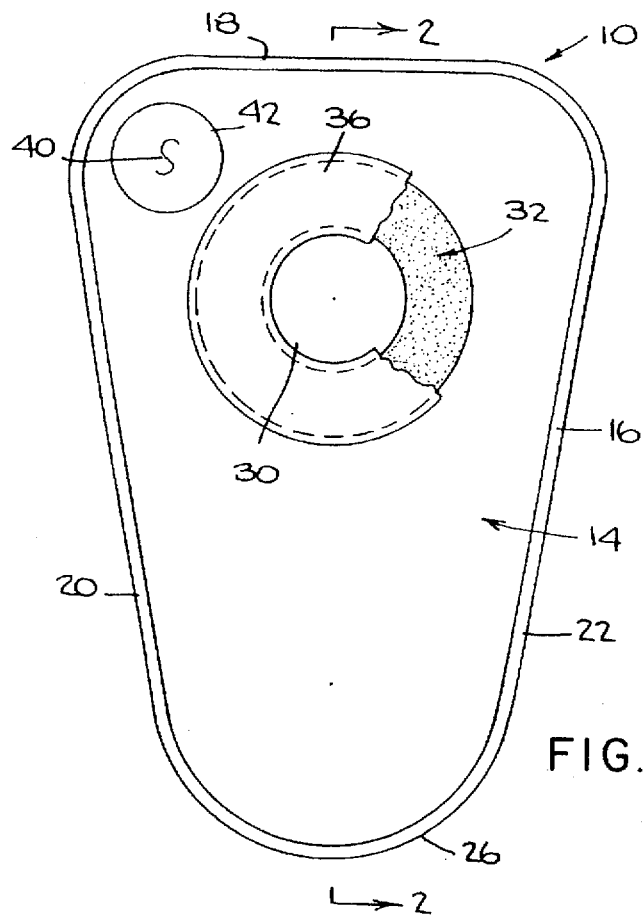
FIG. 1 is a plan view of an ostomy pouch incorporating one embodiment of the invention.
Figure 3:
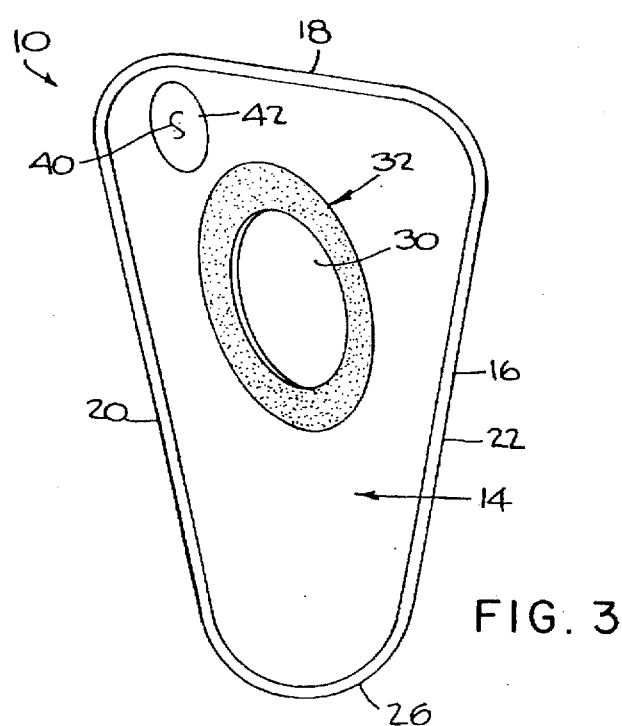
FIG. 3 is a simplified perspective view thereof, with the adhesive face of the support coupling exposed.
Figure 2:
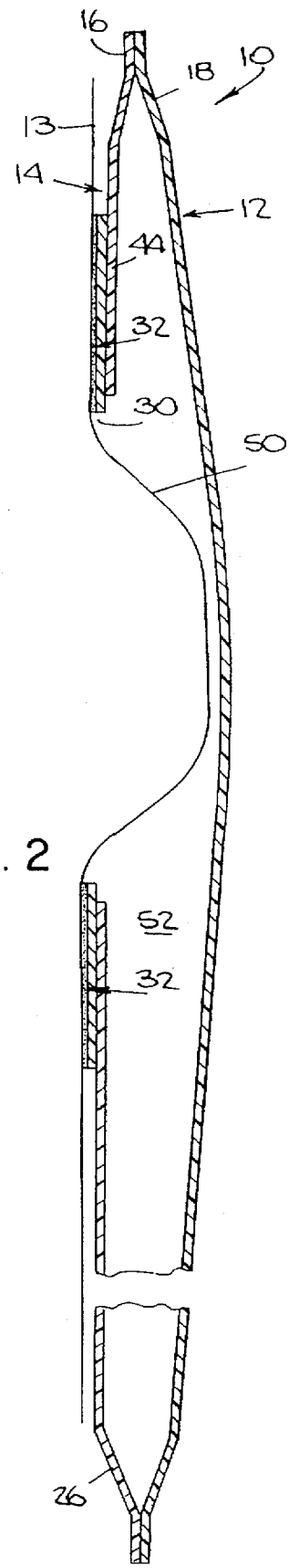
FIG. 2 is a sectional view thereof taken on the line 2—2 of FIG. 1.

An ostomy pouch incorporating one embodiment of the invention is generally indicated by the reference number 10 in FIG. 1. The pouch 10 is formed of a suitable known flexible thermoplastic material that is gas and water impermeable.

The pouch 10 includes a front wall 12 that faces away from the abdomen 13, and a rear wall 14 that confronts the abdomen 13. The front and rear walls 12 and 14 are joined together by a peripheral thermoweld 16 and thus constitute an expandable pouch envelope 12–14. The pouch 10 further includes a top portion 18 with rounded corners, and opposite side portions 20 and 22 that converge from the top portion 18 to a rounded bottom portion 26.

In a preferred embodiment of the pouch 10, the height of the pouch is approximately 7.750 inches, the maximum width of the top portion of the pouch at the rounded corners is approximately 5.125 inches, the bottom portion 26 has a radius of approximately 1.750 inches and the angle of convergence of the side portions 20 and 22 is approximately 15°.

A preferred size range for the pouch 10 is 4.5 to 6 inches maximum width of the pouch, 6 to 8 inches pouch height, and a convergence angle of 15° to 25°.

A waste inlet opening 30 is formed in the rear wall 14 nearer the top portion 18 than the bottom portion 26. The waste inlet opening 30 is bordered by a washer-shaped adhesive coupling wafer 32 approximately 0.010 inches thick, preferably joined to the wall 14 by thermowelding. The adhesive coupling wafer 32 is constituted of a biocompatible bonding material that securely joins the pouch directly to the abdominal surface around the stoma.

A suitable biocompatible bonding material that constitutes the coupling wafer 32 is a hydrocolloid such as Stomahesive®, manufactured by Bristol-Myers Squibb Company. For packaging purposes, the adhesive coupling wafer 32 can be covered with a known silicone release paper 36 that is removed prior to attachment of the pouch 10 to the abdomen.

An S-shaped gas evacuation slit 40 or other suitable gas evacuation outlet is formed in the rear wall portion 14 of the pouch 10 near the top and side edges 18 and 20, offset from the coupling wafer 32. A known generally circular deodorizing filter 42 of the type disclosed in U.S. Pat. No. 5,074,851, is provided at an inside surface 44 of the rear wall 14 in substantial alignment with the gas evacuation slit 40.

In using the ostomy pouch 10, the silicone release paper 36 that covers the wafer 32 is manually removed. It will be noted from FIG. 1 that the silicone release paper 36 can have a larger outside diameter than the coupling wafer 32 to facilitate removal of the release paper 36. The pouch 10 can thus be directly adhered to the abdominal wall 13 with the waste inlet opening 30 aligned with the stoma 50. A leak tight joint is thus established by the pouch 10 around the stoma 50.

Waste material (not shown) that issues from the stoma 50 passes into a waste collection chamber 52 of the pouch 10. When an appropriate amount of waste material accumulates in the collection chamber 52, the pouch 10 is ready for disposal.

Separation of the pouch 10 from the abdominal wall 13 is accomplished by peeling the coupling wafer 32 away from the abdominal wall 13.

The adhesive bond between the coupling wafer 32 and the abdominal wall 13 is of a predetermined strength that resists outward pull-off or slippage of the wafer 32, but permits easy peel off from the abdominal wall 13.

Once the pouch 10 is separated from the abdominal wall 13, it can be flushed down a water-saver toilet, preferably with a carrier bag of the type shown in U.S. Pat. No. 4,830,187. In European wash down water closets, the carrier bag can be omitted but the top portion 18 is preferably cut or ripped to permit evacuation of confined waste during the flushing process.

The pouch 10 is deposited in a toilet, bottom portion first. The convergent shape of the pouch 10, the gauge of the walls 12, 14, and the highly flexible non-obtrusive coupling wafer 32 enable the pouch to flex and flow in streamlined fashion through the toilet passages and sewer pipes. It has been found that flushability of the pouch is enhanced when the pouch has a 15° to 25° angle of convergence and the width and pouch height are in the size ranges previously specified.

Another embodiment of the invention is generally indicated by the reference number 70 in FIG. 4.

The pouch 70 includes a pouch envelope 12–14 identical to the envelope of the pouch 10. The envelope 12–14 of the pouch 70 thus includes the top portion 18, opposite converging side portions 20 and 22, the bottom portion 26 and a waste inlet opening 30 in the rear wall 14.

The waste inlet opening 30 is bordered by a washer-shaped adhesive coupling 72 that frames the waste inlet opening 30. Preferably the washer-shaped coupling 72 is constituted of 3M Plastic Medical Tape on Liner No. 9835 manufactured by the 3M Company of St. Paul, Minn. The coupling tape 72 which is approximately 0.025 mm. thick, includes an acrylate adhesive coating 74 on a coextruded backing that can be ethylene vinyl acetate and polyethylene thermowelded to an outside surface 78 of the rear wall 14.

Referring to FIG. 5, the coupling tape 72 is adapted to join with a coupling film 80, also in the form of a washer, provided on a plastic, generally rectangular abdominal mounting plate 84 (FIG. 5). The abdominal mounting plate 84 is joined in a known manner to the abdominal wall 13 using a suitable biocompatible adhesive such as Stomahesive® bonding material, manufactured by Bristol-Myers Squibb Company.

The coupling film 80 is preferably constituted of 3M Plastic Medical Tape Without Liner No. 1516, manufactured by 3M Company of St. Paul, Minn., and includes a pressure sensitive acrylate adhesive on a polyester film backing. The polyester film backing can be joined to the mounting plate 84 at an annular peripheral zone.

The pouch envelope 12–14 also includes a gas evacuation slit 40 and a deodorizing filter 42.

In using the ostomy pouch 70, the mounting plate 84 is first adhered to the abdominal wall 13 to align a central opening 86 of the mounting plate with the stoma 50. A silicone release paper 36 which normally covers the coupling tape 72 until the pouch 70 is ready for use, is removed to enable the coupling tape 72 to join with the securement film 80 on the mounting plate 84. A leak-tight joint is thus established by the pouch 70 around the stoma 50.

When the pouch 70 is ready for disposal, it can be removed from the abdominal wall 13. The coupling tape 72 is peeled away from the coupling film 80 on the mounting plate 84. The adhesive bond between the coupling tape 72 and the coupling film 80 is of a predetermined strength that resists outward pull off or slippage but permits the coupling tape 72 to be easily peeled from the coupling film 80.

The removed pouch 70, which has the same dimensional relationship as the pouch 10, is deposited in a toilet, bottom portion first. By virtue of the convergent shape of the pouch, the gauge of the walls 12 and 14, the highly flexible and unobtrusive coupling wafer 72 and the predetermined dimensional size range of pouch height, top width and convergence angle enable the pouch to be flushed in substantially risk-free fashion.

Preferably the pouch 70 is flushed with a carrier sleeve of the type shown in U.S. Pat. No. 4,830,187, when deposited in a water-saver toilet. For flush disposal in European wash down toilets, the carrier bag can be omitted and the pouch 70 can be cut or ripped at the top to permit evacuation of confined waste during the flushing process.

As a further option, the pouch 70 with the coupling film 80 can be laminated to a Stomahesive® wafer for direct placement of the Stomahesive® wafer and the pouch 70 as an integral unit directly onto the abdominal wall. When the pouch is ready for disposal it can be peeled from the abdominal wall.

Some advantages of the present invention evident from the foregoing description include an ostomy pouch that is sufficiently flexible to negotiate the passages within a water-saver toilet and a sewer pipe or septic line. The thin walled structure of the pouch envelope and the thin gauge of the adhesive wafer, which does not form an obtrusive structure on the pouch envelope, and the converging optimal V-shape and size of the pouch ensure that the pouch structure itself does not constitute an obstacle to flushability. The pouch thus provides substantially risk-free flush disposal capability.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A flushable ostomy pouch for holding body waste that passes through a stoma comprising:
   a) a pouch formed of flexible plastic sheet material defining a waste collection chamber for body waste that passes through a stoma,
   b) a waste inlet opening formed in said pouch for passage of waste material from said stoma into said collection chamber,
   c) said pouch having a top end portion, a bottom end portion opposite said top end portion, and opposite side edges extending between said top end portion and said bottom end portion, said side edge portions converging toward each other in a direction from said top end portion to said bottom end portion such that said pouch in plan view is substantially V-shaped, and
   d) said pouch having a height of 6 to 8 inches extending from said top end portion to said bottom end portion, a top end portion width of 4.5 to 6 inches, and an angle of convergence of the side portions in the range of 15° to 25°.

2. The ostomy pouch as claimed in claim 1 wherein the angle of convergence of said pouch is approximately 15°, the height is approximately 7.750 inches and the maximum width is approximately 5.125 inches.

3. The ostomy pouch as claimed in claim 1 including bonding means for detachably coupling said envelope around a stoma.

4. The ostomy pouch as claimed in claim 3 wherein said bonding means has a predetermined bond strength that permits said pouch to be peeled as a unit away from said stoma.

5. The ostomy pouch as claimed in claim 3 wherein said bonding means includes an adhesive wafer provided around said waste inlet opening.

6. The ostomy pouch as claimed in claim 5 wherein said adhesive wafer is approximately 0.010 inches thick.

7. The ostomy pouch as claimed in claim 5 wherein said adhesive wafer is washer shaped and has an exposed adhesive surface for adhering said wafer around a stoma.

8. The ostomy pouch as claimed in claim 5 wherein said adhesive wafer is a hydrocolloid adhesive.

9. The ostomy pouch as claimed in claim 5 wherein said adhesive wafer includes a backing layer coated with adhesive, the backing layer being joined to said pouch.

10. The ostomy pouch as claimed in claim 5 wherein said adhesive wafer is formed from an adhesive tape.

11. A waste collection system for an ostomy patient comprising,
   a) a flushable ostomy pouch including an envelope formed of flexible plastic sheet material defining a waste collection chamber for body waste that passes through stoma, a waste inlet opening formed in said envelope for passage of waste material from said a stoma into said collection chamber, flexible annular adhesive coupling means on said envelope around said waste inlet opening for positioning said waste inlet opening around a stoma, said coupling means being constituted of an adhesive coupling tape having an exposed adhesive coating and a backing layer for said coating in surface contact with said envelope, said pouch being V-shaped and having a height of 6 to 8 inches from said top end portion to said bottom end portion, a width at the top end portion of 4.5 to 6 inches and an angle of convergence of the side edge portions of 15° to 25°, and
   b) an abdominal mounting plate having an outside surface and an obverse surface, and formed with a stoma engagement opening for securement with said adhesive coupling tape, and a bonding material for attachment of said mounting plate to an abdominal surface.

12. A method for facilitating flush disposal of an ostomy pouch comprising, a) forming a pouch of flexible plastic sheet material with a waste inlet opening and a waste collection chamber, and limiting the height of the pouch from 6 to 8 inches, the width of the pouch at the top end portion from 4.5 to 6 inches and the angle of convergence of the side end portions in the range of 15° to 25°, and b) providing an adhesive approximately 0.010 inches thick around the waste inlet opening to secure the envelope directly to the abdomen with the waste inlet opening aligned with a stoma.

* * * * *